United States Patent
Deemer et al.

(10) Patent No.: US 7,617,733 B2
(45) Date of Patent: Nov. 17, 2009

(54) METHOD AND APPARATUS FOR ULTRASOUND PHASED ARRAY TESTING OF BEARING BALLS

(75) Inventors: Christopher M. Deemer, Woodridge, IL (US); William A. Ellingson, Naperville, IL (US); J. Scott Steckenrider, Jacksonville, IL (US)

(73) Assignee: UChicago Argonne, LLC, Chicago, IL (US)

(*) Notice: Subject to any disclaimer, the term of this patent is extended or adjusted under 35 U.S.C. 154(b) by 277 days.

(21) Appl. No.: 11/779,677

(22) Filed: Jul. 18, 2007

(65) Prior Publication Data

US 2009/0019937 A1  Jan. 22, 2009

(51) Int. Cl.
G01N 29/00 (2006.01)

(52) U.S. Cl. ............... 73/660; 73/593; 73/628; 73/641

(58) Field of Classification Search .......... 73/593, 73/620, 622, 627, 629, 637, 638, 640, 641, 73/642, 644
See application file for complete search history.

(56) References Cited

U.S. PATENT DOCUMENTS

| | | | |
|---|---|---|---|
| 4,044,321 A * | 8/1977 | Vasile | 333/194 |
| 5,001,674 A | 3/1991 | Kawasaki | |
| 5,056,368 A | 10/1991 | Kawasaki et al. | |
| 5,184,513 A * | 2/1993 | Nishioka et al. | 73/593 |
| 5,195,372 A | 3/1993 | Fushimi et al. | |
| 5,305,755 A * | 4/1994 | Nakao | 600/472 |
| 6,843,131 B2 * | 1/2005 | Graff et al. | 73/622 |
| 6,886,407 B1 * | 5/2005 | Fredenberg | 73/622 |
| 7,428,842 B2 * | 9/2008 | Fair et al. | 73/626 |
| 2005/0126291 A1 * | 6/2005 | Czerw et al. | 73/589 |
| 2007/0068257 A1 * | 3/2007 | Belahcene et al. | 73/597 |
| 2007/0119255 A1 * | 5/2007 | Czerw et al. | 73/621 |

FOREIGN PATENT DOCUMENTS

| | | | |
|---|---|---|---|
| JP | 07244028 A | * | 3/1994 |
| WO | PCT/EP00/00348 | | 1/2000 |

* cited by examiner

*Primary Examiner*—J M Saint Surin
(74) *Attorney, Agent, or Firm*—Joan Pennington

(57) ABSTRACT

An automated scanning system and method, utilizing specialized dual phased array ultrasonic transducers for producing and detecting Rayleigh waves in ceramic bearing balls are provided for nondestructive, non-contact inspection of ceramic bearing balls. The phased array ultrasonic transducer utilizes a complex curvature configuration that enables the dual phased array ultrasonic transducers to focus ultrasonic energy onto the ball to optimally generate and receive Rayleigh wave signals in the spherical objects.

20 Claims, 3 Drawing Sheets

METHOD AND APPARATUS FOR ULTRASOUND PHASED ARRAY TESTING OF BEARING BALLS

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

The present invention relates to a method and apparatus for the nondestructive evaluation (NDE) of bearing balls, and more particularly to a method and apparatus for the detection and characterization of Hertzian C-cracks in ceramic bearing balls.

DESCRIPTION OF THE RELATED ART

For many advanced applications conventional metal bearings are inappropriate, for example, due to the requirement for lubrication and the reduced performance at high temperatures. Ceramic bearing balls overcome these limitations but are susceptible to defect-induced failure. Most critical defects occur near the surface where highest stresses are produced.

Hertzian C-cracks, or "cone-cracks", so-called because of their "C" shape appearance on the surface, are in reality a subsurface crack usually in the shape of a cone, hence these are also known as "cone cracks". These cracks are usually induced by ball to ball contact during processing and handling. Once the crack is large enough, and spallation of the cracked zone occurs, the life and performance of the bearing system is compromised. In many applications, such as shaft bearings for power generation or propulsion gas turbine engines, failure of a bearing system could have catastrophic results.

In order to reduce the potential for failure and reduce the risk for application, it is essentially mandatory to have a cost-effective non-destructive inspection system to detect any possible existing crack on any ball of any size. Presently, there is one known system in the world that is accepted for inspection of these bearing balls. This system utilizes three conventional piezoelectric (PZT) ultrasonic transducers for Rayleigh waves to detect the C-cracks. This system utilizes a very complex bearing ball handling mechanism and has a low signal to noise ratio, which makes accurate C-crack detection difficult.

U.S. patents have been issued which also address the problem at hand as follows:

U.S. Pat. No. 5,001,674 issued Mar. 19, 1991 to Kawasaki, and entitled "Ultrasonic Testing Method" discloses an ultrasonic testing method comprises steps of transmitting an ultrasonic wave from a probe to a test article, detecting an internal flaw in the test article by a reflected flaw echo from the internal flaw, and deciding a condition of the detected flaw by comparing and analyzing frequency components of the transmitted ultrasonic wave and the reflected flaw echo. The probe has a curved tip surface, which is the same kind as that of a curved incident surface of the test article and has a radius of curvature of 0.5 about 2.0 times the radius of curvature of the curved incident surface of the test article.

U.S. Pat. No. 5,001,674 issued Oct. 15, 1991 to Kawasaki et al., and entitled "Ultrasonic Testing Method" discloses an ultrasonic testing method for detection of flaws in a material to be tested having a curved surface portion by use of an ultrasonic probe, wherein a center axis of curvature of the curved surface portion of the material to be tested and the center axis of the probe are set in an eccentric relationship so that the angle of refraction of an ultrasonic wave is 90°, and the probe comprises a tip portion having a curved surface of the same kind as the curved surface portion of the material to be tested and a radius of curvature of from 1.0 to 3.0 times the radius of curvature of the curved surface portion of the material to be tested. The method enables detection of internal flaws in, particularly, a spherical or cylindrical body formed of a ceramic and used as a bearing member.

U.S. Pat. No. 5,195,372 issued Mar. 23, 1993 to Fushimi et al., and entitled "Ultrasonic Testing Method for detecting flaws of balls for structural members and apparatus for said method" discloses an ultrasonic testing method for detecting flaws of balls for structural members comprises rotating a ball to be tested in an ultrasonic wave transmitting medium. At least two focus-type ultrasonic probes are provided and arranged so as to cover nonoverlapping flaw-detecting regions on and/or inside the ball. Flaws in the ball are detected by sending ultrasonic waves from the probes toward the ball. An apparatus for detecting flaws of balls comprises a ball holding portion for rotatably holding the ball to be tested, at least two focus-type probes for detecting flaws and at least two probe mounting portions for mounting the probes thereof so that respective axes of the probes are each capable of being set eccentrically relative to the center of the ball and wherein the focal positions of the probes are variable.

PCT Patent No. WO 00/43769 entitled: "Device and Method for Testing Bearing Elements Using Ultrasound issued Jul. 27, 2000, which is available in German, discloses a device and method for the in-series, non-destructive ultrasonic testing of ceramic bearing elements (rollers and balls) for defects >50 μm (micro-meters). The method provides for the transport of the test pieces throughout, the test itself and the evaluation of the test. At least two ultrasonic testing heads are used to take the necessary measurements at various azimuth angles at the same time. During the measuring process, the ball rotates about an axis of rotation at the same time as the ultrasonic testing heads are pivoted about the pivot axis, which is arranged perpendicular thereto.

Important aspects of the present invention are to provide an improved method and apparatus for ultrasonic phased array testing of bearing balls, to provide such improved method and apparatus for ultrasonic phased array testing of bearing balls substantially without negative effect and that overcome some of the disadvantages of prior art arrangements.

SUMMARY OF THE INVENTION

In brief, a method and apparatus for ultrasonic phased array testing of bearing balls are provided. The present invention provides an automatic scanning system for nondestructive, non-contact inspection of ceramic bearing balls, utilizing specialized dual phased array ultrasonic transducers or probes for producing and detecting surface acoustic waves in the ceramic bearing ball under test. For example, a Rayleigh wave is generated, which is a wave similar to a seismic wave in that it propagates on the surface of a solid. The phased array ultrasonic transducer utilizes a complex curvature configuration that enables the sensor to focus ultrasonic energy onto the ball to optimally generate and receive Rayleigh wave signals in the spherical objects Each element in the probes produces a wave that radiates generally in all directions from the surface of the probe. When the phased-array respective transducer is fired toward a ball, highest energy density portion of the wave produced by the respective ultrasonic transducer element contacts the bearing ball generally at the Rayleigh wave critical angle and some point on the surface to the ball (point $P_i$) independent of the location of the respective element on the transducer.

In accordance with features of the invention, the dual transducer design is fixtured to a mount that enables the system to probe a 90-degree arc around the ball while the ball sits on a rapidly rotating pedestal. The system utilizes a pair of 32 element transducers, for a total of 64 elements. The first of the probes generates and detects waves from the upper hemisphere, while the second covers the lower hemisphere. Therefore, the entire ball is scanned by rotating the ball 360-degrees.

In accordance with features of the invention, rapid and low-cost detection of defects are enabled, for example, with inspection taking less than one minute per ball. Surface acoustic waves or Rayleigh waves are used in a pulse echo mode for rapid surface inspection.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, a method and apparatus are provided for the nondestructive evaluation (NDE) of bearing balls. The invention provides a method and apparatus for the detection and characterization of surface breaking cracks in ceramic bearing balls. The invention overcomes limitations of prior art systems that utilize a very complex bearing ball handling mechanism and have a low signal to noise ratio which makes accurate C-crack detection difficult.

Ultrasonic surface acoustic waves, also called Rayleigh waves, are defined as a guided wave that propagates along the surface of a medium. Like other guided waves (such as Lamb waves), surface acoustic waves (SAWs) travel in the lateral direction, and propagate along the materials surface. Their use for NDE is a single-sided technique. This makes SAWs an attractive means of detecting defects that are perpendicular to a material's surface, such as surface breaking cracks. Surface acoustic waves are suitable for surface breaking cracks because the energy of the waveform is concentrated at the surface. The SAW travels along the surface, but its amplitude decays within the material. The amount of decay is governed by the frequency of the wave.

The decay depth is on the order of the wavelength of the propagating waveform. The asymptotic decay of the waveform amplitude means that the majority of the wave's energy is contained within a single wavelength from the material's surface.

A SAW can be generated by a longitudinal ultrasonic transducer by positioning the transducer at a critical angle with respect to the local surface normal. If a surface breaking crack is present in the propagation path of the SAW, a portion of the waveform's energy is reflected and can be detected by the transducer in the pulse echo mode. As the wave propagates along the surface, SAWs can be used on non-planar geometries, such as pipes and weld radii.

In accordance with features of the invention, a dual-probe transducer design is provided to ensure complete ball coverage. The two probes are positioned in line perpendicular to the axis of the ball, for example, as illustrated and described with respect to FIG. 3. The transducers produce Rayleigh waves in opposite directions. Each transducer is capable of detecting defects at a distance equivalent to one-quarter the ball circumference. Rotation of the ball about the axis shown in FIG. 3 during data acquisition provides full ball coverage with a single bearing ball rotation stage.

Figure 1:
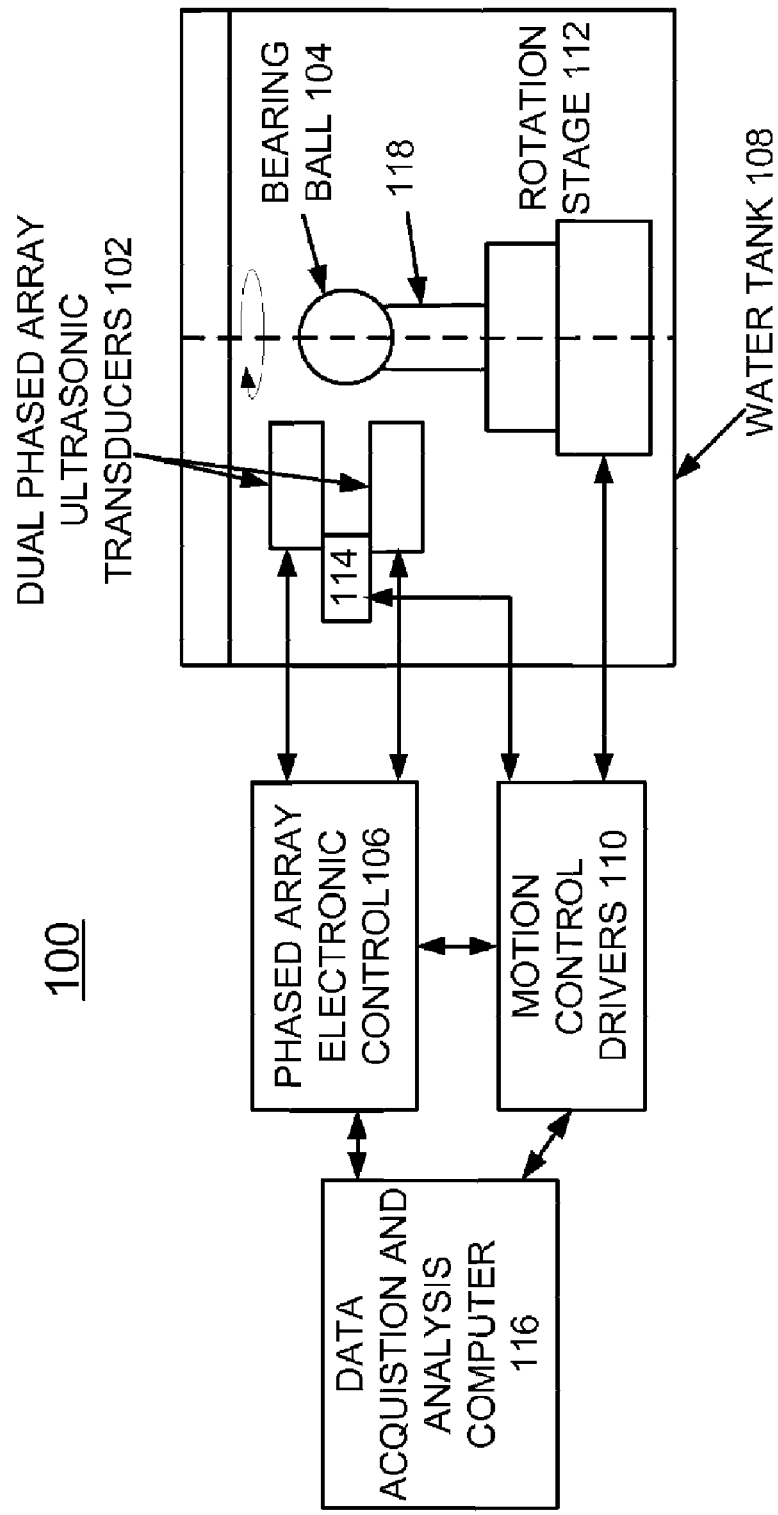
FIG. 1 is a block diagram illustrating an exemplary bearing ball testing system in accordance with the preferred embodiment.

Having reference now to the drawings, in FIG. 1 there is shown an exemplary bearing ball testing system in accordance with the preferred embodiment and generally designated by the reference numeral 100. Bearing ball testing system 100 is an automatic scanning system for nondestructive non-contact inspection of ceramic bearing balls, which utilizes specialized dual phased array ultrasonic transducers 102 for producing and detecting Rayleigh waves in ceramic bearing balls.

The dual phased array ultrasonic transducers or probes 102 utilize a complex curvature configuration that enables the probes 102 to focus ultrasonic energy onto a bearing ball 104 being tested to optimally generate and receive Rayleigh wave signals in such spherical objects.

Bearing ball testing system 100 includes a phased array electronic control 106 in accordance with the preferred embodiment that controls the dual phased array ultrasonic transducers 102 for producing and detecting Rayleigh waves in the ceramic bearing ball 104 under test. A water tank 108 contains the dual phased array ultrasonic transducers 102 and the ceramic bearing ball 104 under test.

Bearing ball testing system 100 includes motion control drivers 110 coupled to a rotation stage 112 for the ceramic bearing ball 104 under test and a mount 114 for positioning and moving or rotating the position of the dual phased array ultrasonic transducers 102 relative to the ceramic bearing ball 104 under test. The phased array electronic control 106 is coupled to the motion control drivers 110 controlling sequential firing and detection of elements or ultrasonic transducers of the dual phased array ultrasonic transducers 102 and providing synchronous operation with the rotation stage 112 rotating the bearing ball 104.

Bearing ball testing system 100 includes a data acquisition and analysis computer 116 coupled to the phased array electronic control 106 and motion control drivers 110 operatively controlling the phased array electronic control 106 and the motion control drivers 110 for generating and acquiring test data, and controlling the two motion stages 112, 114 to ensure the entire surface of bearing ball is covered. The data acquisition and analysis computer 116 processes the test data to identify a defect in the bearing ball 104 under test.

The dual phased array ultrasonic transducers 102 are fixtured to the mount 114 that enables the system 100 to probe a 180 degree arc around the ball 104 while the ball sits on a rapidly rotating pedestal 118. Surface acoustic waves (SAWs) travel in the direction of the surface and are generated by the ultrasonic transducers 102 by positioning the transducer at a critical angle with respect to the local surface normal.

In accordance with features of the invention, the dual specialized phased arrays of a plurality of ultrasonic transducers 102 are provided for optimizing generation and detection of Rayleigh waves in bearing balls. In the system 100 of the invention, each ultrasonic transducer or element of the dual phased array ultrasonic transducers 102 produces a wave that radiates in all directions from the surface of the probe. When the phased-array transducer is fired toward a ball, a portion of the longitudinal waves produced by element i will contact the ball at the Rayleigh wave critical angle at some point on the surface to the ball (point $P_i$) independent of the location of element i on the transducer.

In accordance with features of the invention, a location $P_i$ on the ball's surface and the time that it takes the Rayleigh wave to propagate to a point $P_{i+1}$ are computed. By using the phased array electronic control 106 for providing a delay in firing times of element i and a next element i+1 equal to the difference between the time required for the longitudinal wave produced by element i+1 to reach $P_{i+1}$ and the time required for the longitudinal wave produced by element i to reach point $P_i$ and then propagates as a Rayleigh wave from $P_i$ to $P_{i+1}$, the signal of the Rayleigh wave is increased due to the superposition of the two waves, generated at $P_i$ and $P_{i+1}$. This signal advantageously is expanded on by using the phased array electronic control 106 for firing all n elements, each with an appropriate delay, to produce a Rayleigh wave with larger amplitudes than obtained with waveforms generated with a single element. Timing is reversed to detect wave reflected from any defect and the bearing ball surface. By utilizing phased-array technology of the phased array electronic control 106, the signal strengths of the Rayleigh waves are larger and result in higher detection sensitivity than a system using a single element.

Figure 2:
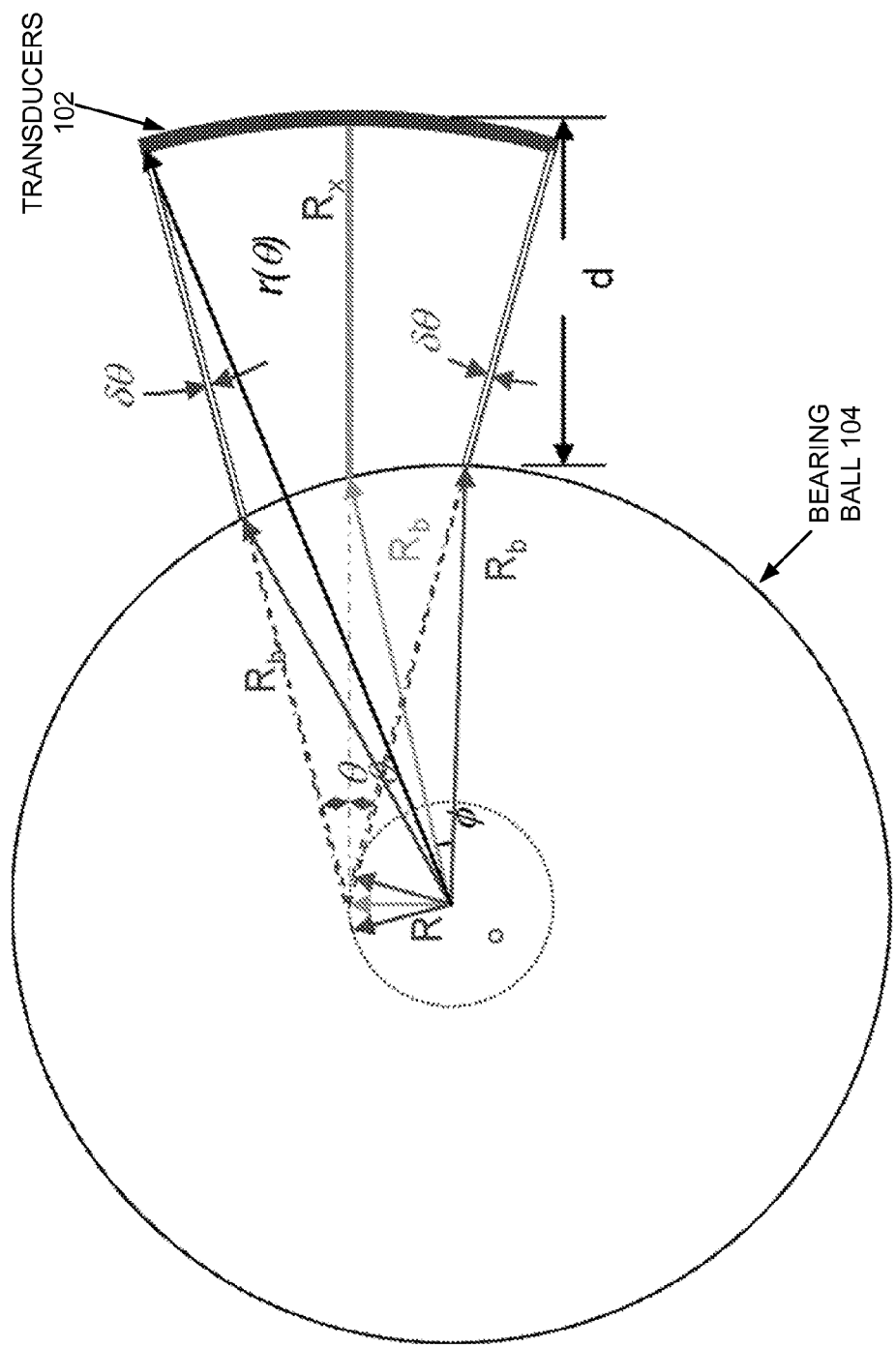
FIG. 2 is a schematic diagram illustrating a curvature of an exemplary transducer relative to the surface of a bearing ball in accordance with the preferred embodiment.
Figure 3:
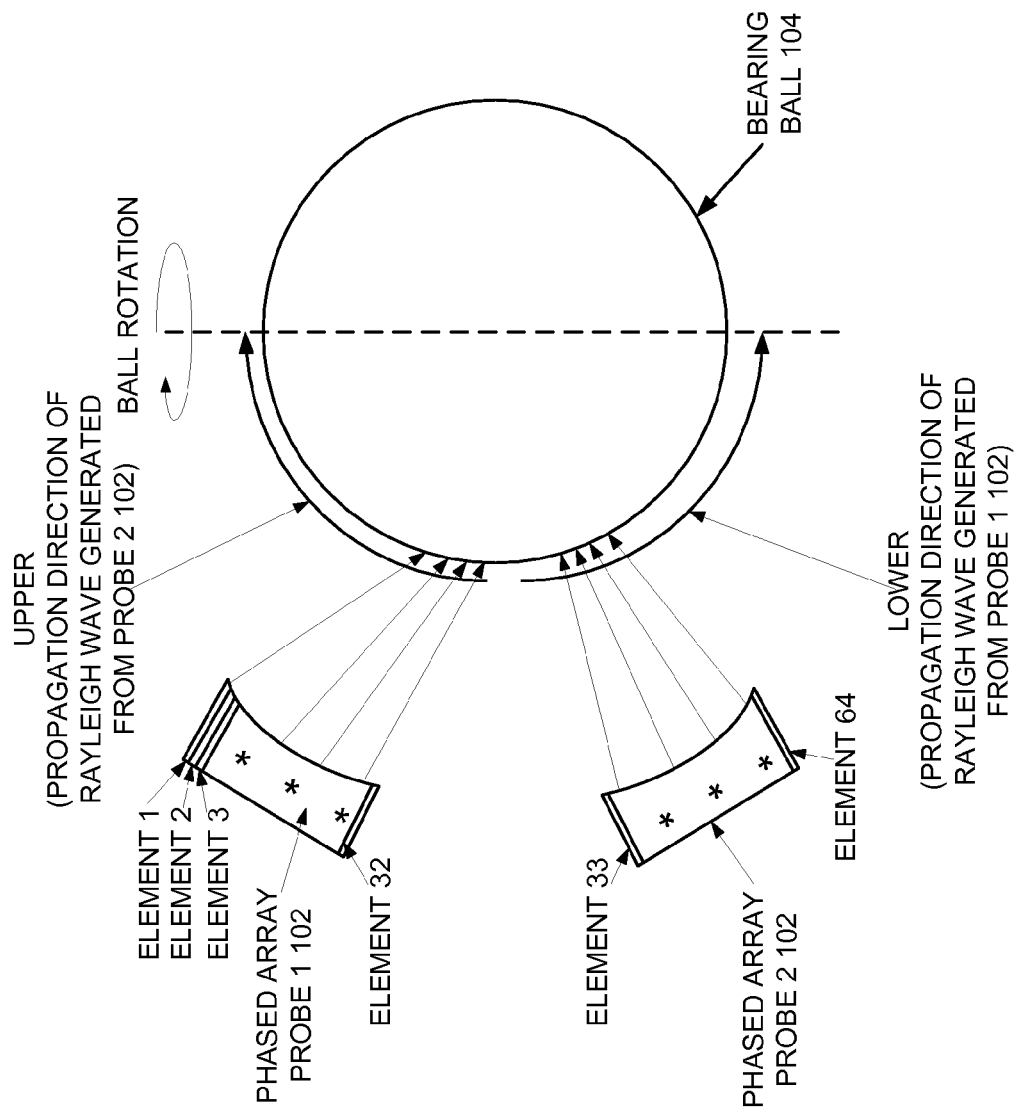
FIG. 3 is a schematic diagram illustrating operation of the exemplary bearing balls testing system of FIG. 1 with dual-probe transducer for full-ball coverage with a single rotation stage in accordance with the preferred embodiment.

Referring now to FIGS. 2 and 3, operation of system 100 may be understood with the dual phased array ultrasonic transducers 102 of the preferred embodiment.

System 100 utilizes, for example, a pair of 32 element transducers 102 with 64 elements total, for example, designed to avoid the loss of energy caused by a conventional energy profile resulting from individual elements that are not optimized at a critical angle with respect to the local surface normal. The dual phased array ultrasonic transducers 102 was optimized for Rayleigh wave generation in 1-in.-diameter balls; however changing the ball diameter will cause only a slight loss of the energy in the waveforms.

A complex curvature incorporated into the design of dual phased array ultrasonic transducers 102 allows for the maximum energy transfer from the transducer into a Raleigh wave in the sample 104 by ensuring that the local normal of the transducers facing the ball 104 at the Raleigh-wave critical angle, see FIG. 2. The geometry of the dual phased array ultrasonic transducers 102 was designed so that the wave produced off the surface normal of each element will contact the ball 104 at the Rayleigh-wave critical angle. By ensuring that each element's surface normal generally intersects the ball 104 at the Rayleigh-wave critical angle, the transducer 102 is optimized for maximum signal generation and detection.

FIG. 2 illustrates an exemplary curvature of transducer 102 relative to the surface of a bearing ball 104 in accordance with the preferred embodiment. The curvature of transducer 102 is provided to focus the beam onto the surface of the bearing ball 104, cylindrical. The curvature of transducer 102 is provided to keep the transducer face normal to the ray hitting the bearing ball surface at a critical angle: a linear spiral. This geometry has been approximated as a concave sphere for the sake of manufacturing ease.

As shown in FIG. 2, illustrated labels are defined as follows
$R_b$ represents Ball radius;
$R_x$ represents Transducer radius;
$R_o$ represents $R_b \sin(\phi)$;
d represents Transducer standoff; and where r (θ) is defined by:

$$r(\theta) = ((R_o^2 + R_x^2) - (2R_o R_x \cos(90+\theta)))^{1/2}$$

An optimal geometry of the transducer 102 was found to be a linear spiral. This geometry did not have a close form solution, and manufacture of such a shape was found to be expensive and time consuming.

As illustrated in FIG. 2, an optimal geometry in accordance with the invention was approximated as a concave sphere. The difference of the surface normal between the two geometries relative to the balls surface was only 0.5°. By ensuring that each element's surface normal will intersect the ball 104 within 0.5° of the Rayleigh-wave critical angle, the transducer 102 is optimized for maximum signal generation and detection.

Note that while the geometry of the dual 32-element ultrasonic transducer probe 102 was optimized for 1-in.-diameter balls, it is possible to use this probe with different diameters. FIG. 3 illustrates operation of the exemplary bearing ball testing system 100 with dual-probe transducers 102 providing full-ball coverage with a single rotation stage 112 in accordance with the preferred embodiment.

The two probes 1, 2, 102 are positioned in line perpendicular to the axis of the ball 104 on the same side of the ball. The transducers produce Rayleigh waves in opposite directions. Each transducer is capable of detecting defects at a distance equivalent to one-quarter the ball circumference, and the dual-probe design ensures that 180° of the ball circumference will be covered.

Rotation of the ball about the axis shown in FIG. 3 during data acquisition provides full ball coverage with a single rotation stage 112. To account for crack orientation, the motion system is designed with the second stage 114, which rotates the transducer mounting system. By rotating the position of the probes 102 on an axis orthogonal to the ball's rotation axis, the cracks can be detected independent of the defect's orientation or the placement of the ball 104 in the scanning system. The motion system is a great advantage of the bearing ball scanning test system 100 because it only requires two motion stages 112, 114 and ensures that the entire ball's surface is covered.

While the present invention has been described with reference to the details of the embodiments of the invention shown in the drawing, these details are not intended to limit the scope of the invention as claimed in the appended claims.

What is claimed is:

1. An apparatus for ultrasonic phased array testing of bearing ball comprising:
    a plurality of phased arrays of ultrasonic transducers; each ultrasonic transducer having a defined curvature to focus ultrasonic enemy at a critical angle onto the bearing ball, optimizing signal generation and detection;
    a mount positioning and moving said phased arrays of ultrasonic transducers relative to a bearing ball under test;
    a rotation stage rotating the bearing ball under test about an axis;

a phased array electronic control coupled to said phased arrays of ultrasonic transducers controlling sequential firing and detection of ultrasonic transducers of said phased arrays with the ultrasonic energy produced by said ultrasonic transducers being converted into a surface acoustic wave propagating along a bearing ball surface with enhanced amplitude; and a data acquisition and analysis computer coupled to said phased array electronic control generating and acquiring test data, and processing the test data to identify a defect in the bearing ball under test.

2. The apparatus for ultrasonic phased array testing of bearing ball as recited in claim 1 includes an automated motion system including motion control drivers coupled to said phased array electronic control and said data acquisition and analysis computer.

3. The apparatus for ultrasonic phased array testing of bearing ball as recited in claim 2 wherein said motion control drivers control movement of said mount for positioning and moving said phased arrays of ultrasonic transducers relative to the bearing ball under test.

4. The apparatus for ultrasonic phased array testing of bearing ball as recited in claim 2 wherein said motion control drivers control said rotation stage for rotating the bearing ball under test about an axis.

5. The apparatus for ultrasonic phased array testing of bearing ball as recited in claim 1 includes a water tank containing said phased arrays of ultrasonic transducers and the bearing ball under test.

6. The apparatus for ultrasonic phased array testing of bearing ball as recited in claim 1 wherein said phased arrays of ultrasonic transducers are positioned in a line to produce waves that propagate perpendicular to the axis of rotation of the bearing ball under test.

7. The apparatus for ultrasonic phased array testing of bearing ball as recited in claim 1 wherein each of said phased arrays of ultrasonic transducers enables detecting defects at a distance approximately equivalent to one-quarter the circumference of the bearing ball under test.

8. The apparatus for ultrasonic phased array testing of bearing ball as recited in claim 1 wherein said phased arrays of ultrasonic transducers are moved along a line relative to the bearing ball under test during the rotation axis of the bearing ball under test.

9. The apparatus for ultrasonic phased array testing of bearing ball as recited in claim 1 wherein said phased arrays of ultrasonic transducers include dual phased arrays of ultrasonic transducers.

10. The apparatus for ultrasonic phased array testing of bearing ball as recited in claim 9 wherein said dual phased arrays of ultrasonic transducers include dual 32-element phased arrays.

11. The apparatus for ultrasonic phased array testing of bearing ball as recited in claim 1 wherein said defined curvature of said phased arrays of ultrasonic transducers include a concave sphere.

12. The apparatus for ultrasonic phased array testing of bearing ball as recited in claim 1 wherein said defined curvature of said phased arrays of ultrasonic transducers is optimized for maximum signal generation and detection for a predetermined diameter of the bearing ball under test.

13. A method for ultrasonic phased array testing of bearing ball comprising the steps of:
    providing in a water tank receiving a pair of phased arrays of ultrasonic transducers and a bearing ball under test;
    positioning said pair of phased arrays of ultrasonic transducers relative to the bearing ball under test; each ultrasonic transducer having a defined curvature to focus ultrasonic energy at a critical angle onto the bearing ball, optimizing signal generation and detection;
    rotating the bearing ball under test about an axis;
    providing a phased array electronic control coupled to said pair of phased arrays of ultrasonic transducers to control sequential firing and signal detection of said ultrasonic transducers of said pair of phased arrays with the ultrasonic enemy produced by said ultrasonic transducers being converted into a surface acoustic wave propagating along a bearing ball surface with enhanced amplitude; and
    providing a data acquisition and analysis computer coupled to said phased array electronic control for generating and acquiring test data, and processing the test data to identify a defect in the bearing ball under test.

14. The method for ultrasonic phased array testing of bearing ball as recited in claim 13 includes implementing automated motion control using a plurality of motion control drivers coupled to said phased array electronic control and said data acquisition and analysis computer.

15. The method for ultrasonic phased array testing of bearing ball as recited in claim 13 includes controlling movement of said mount for positioning and moving said phased arrays of ultrasonic transducers relative to a bearing ball under test with one of said motion control drivers.

16. The method for ultrasonic phased array testing of bearing ball as recited in claim 13 includes controlling rotation of the bearing ball under test with one of said motion control drivers.

17. The method for ultrasonic phased array testing of bearing ball as recited in claim 13 wherein positioning said pair of phased arrays of ultrasonic transducers relative to the bearing ball under test includes positioning said phased arrays of ultrasonic transducers in a line generally perpendicular to the axis of the bearing ball under test.

18. The method for ultrasonic phased array testing of bearing ball as recited in claim 13 wherein providing said phased array electronic control coupled to said pair of phased arrays of ultrasonic transducers to control sequential firing and signal detection of said ultrasonic transducers of said pair of phased arrays includes positioning said phased arrays of ultrasonic transducers in a line generally perpendicular to the rotation axis of the bearing ball under test.

19. The method for ultrasonic phased array testing of bearing ball as recited in claim 13 includes providing a concave sphere for said defined curvature of said phased arrays of ultrasonic transducers.

20. The method for ultrasonic phased array testing of bearing ball as recited in claim 13 includes utilizing said pair of phased arrays of ultrasonic transducers for producing and detecting Rayleigh waves in ceramic bearing balls.

* * * * *